United States Patent
Hausheer et al.

(10) Patent No.: US 6,525,037 B1
(45) Date of Patent: Feb. 25, 2003

(54) METHOD OF TREATING ATHEROSCLEROSIS AND COMPLICATIONS RESULTING THEREFROM

(75) Inventors: Frederick H. Hausheer, Boerne; Seetharamulu Peddaiahgari, San Antonio, both of TX (US)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 0 days.

(21) Appl. No.: 09/513,540

(22) Filed: Feb. 25, 2000

(51) Int. Cl.[7] .................... A61K 31/66; A61K 31/255; A61K 21/105
(52) U.S. Cl. .................... 514/127; 514/126; 514/517; 514/707
(58) Field of Search .................... 514/126, 127, 514/517, 707

(56) References Cited

U.S. PATENT DOCUMENTS 5,981,602 A * 11/1999 Tatarintsev et al. ......... 514/707

* cited by examiner

*Primary Examiner*—Theodore J. Criares
(74) *Attorney, Agent, or Firm*—Thomas J. Dodd

(57) ABSTRACT

This invention relates to a method of treating patients afflicted with atherosclerosis or to prevent the development of atherosclerosis in patients assessed to be high risk of developing the disease. The method includes administering to a patient in need of treatment an effective amount of a thiol or reducible disulfide compound according to the formula set forth in the specification.

4 Claims, No Drawings

METHOD OF TREATING ATHEROSCLEROSIS AND COMPLICATIONS RESULTING THEREFROM

FIELD OF THE INVENTION

This invention relates to a method for treating a patient suffering from atherosclerosis, or from complications caused thereby. The method involves administering an effective amount of a disulfide or thiol-containing compound to a patient suffering from atherosclerosis or from complications of atherosclerosis.

BACKGROUND OF THE INVENTION

Atherosclerosis is a common disease that stems from the build up of fatty/cholesterol plaques on the endothelial cells of arteries. The deposits mitigate thickening and stiffening of arterial tissue, with concomitant systemic or localized disorders that result from lessened blood flow. This condition often results in local ischemia, formation of thrombi, embolism due to plaque rupture, and other serious conditions, and can lead to stroke, myocardial infarction, and other life-threatening complications.

Many diverse factors, both internal and external, are thought to be responsible for the gradual onset of atherosclerosis. One of these factors is an abnormally high blood level of homocysteine. High homocysteine levels are a likely consequence of B-vitamin and/or folic acid deficiency and are also associated with reduced renal function. Often, high homocysteine levels are associated with inborn errors of amino acid metabolism.

Current methods of treating atherosclerosis depend upon the severity and location of the problem blood vessels. Particularly with the arteries of the heart, surgery is often employed to break up the deposits. Diuretics and other agents are also administered to reduce the potential serious effects of the disease.

The current methods of treating atherosclerosis carry associated risks of side effects, and are at times unsuccessful in alleviating the problem. Particularly if the underlying cause is excessive homocysteine, the deposits often recur after surgery, and many blood thinners possess potentially serious side effects as well as having no effect on the actual atheromatous deposits themselves.

Homocysteine is a transmethylated derivative of the naturally occurring amino acid methionine, a product of protein metabolism, and has the following structure-

HS—CH$_2$—CH$_2$—CH (NH) —COOH.

Current health literature is replete with references to the desirability of lowering plasma levels of homocysteine. Many publications suggest that homocysteine levels can be safely reduced by increased intake of B-vitamins and folic acid.

Mesna (sodium 2-mercaptoethene sulfonate) and dimesna (disodium 2,2'-dithiobis ethane sulfonate) are known therapeutic compounds that have heretofore demonstrated a wide variety of therapeutic uses. Both mesna and dimesna have been shown to be effective protective agents against certain specific types of toxicity associated with the administration of cytotoxic drugs used to treat patients for various types of cancer.

In particular, mesna has been used with some success in mitigating the toxic effects of cytotoxic agents such as ifosfamide, oxazaphosphorine, melphalane, cyclophosphamide, trofosfamide, sulfosfamide, chlorambucil, busulfan, triethylene thiophosphamide, triaziquone, and others, as disclosed in U.S. Pat. No. 4,220,660, issued Sept. 2, 1980.

The near absence of toxicity of dimesna further underscores the usefulness of this compound, as large doses can be given to a patient without increasing the risk of adverse effects from the protective agent itself.

Further, pharmacological profiles of each compound indicate that, if proper conditions are maintained, mesna and dimesna do not prematurely inactivate primary therapeutic drugs to a significant degree. Thus, neither compound will significantly reduce activity of the chemotherapeutic agent, and in many cases, act to potentiate the effect of the main drug on targeted cancer cells.

The molecular structures of both mesna and dimesna are shown below as Structure I and Structure II respectively.

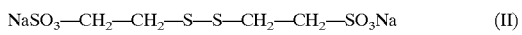

HS—CH$_2$—CH$_2$—SO$_3$Na     (I)

NaSO$_3$—CH$_2$—CH$_2$—S—S—CH$_2$—CH$_2$—SO$_3$Na     (II)

As shown, dimesna is a dimer of mesna, with the optimum conditions for oxidation occurring in the slightly basic (pH ~7.3), oxygen rich environment found in blood plasma. In mildly acidic, low oxygen conditions, in the presence of a reducing agent such as glutathione reductase, conditions prevalent in the kidneys, the primary constituent is mesna.

Mesna acts as a protective agent for a number of cytotoxic agents by substituting a nontoxic sulfhydryl moiety for a toxic hydroxy (or aquo) moiety. This action is particularly evidenced in the coadministration of mesna and oxazaphosphorine, and in the administration of dimesna along with certain platinum agents and/or taxanes.

Dimesna, as well as some analogues, have excellent toxicity profiles in mammalian species. In fact, dimesna has been administered intravenously to mice and dogs in doses higher than the accepted oral LD$_{50}$ for common table salt (3750 mg/kg), with no adverse effects. Dimesna has also been administered to humans in doses exceeding 40 g/m$^2$, with no adverse effects.

Mesna, and other analogues with free thiol moieties, constitute the more physiologically active form of the two types of compounds described in this specification. These compounds manifest their activity by providing free thiol moieties for terminal substitution at locations where a terminal leaving group of appropriate configuration, usually a hydroxy, aquo or superoxide is located. Mesna also tends to form conjugates with naturally occurring biochemicals that contain a free thiol moiety, such as cysteine, glutathione, homocysteine, and others.

Dimesna and other disulfides can be activated intracellularly by glutathione reductase, a ubiquitous enzyme, thereby generating high concentrations of intracellular free thiols. These free thiols act to scavenge the free radicals and other nucleophilic compounds often responsible for causing cell damage.

This profile is especially significant in explaining the success of dimesna in controlling and mitigating the toxic effects of platinum complex antitumor drugs. The mechanism for action in the case of cisplatin (cis-diammine dichloro platinum) is explained in U.S. Pat. No. 5,789,000, which is incorporated herein by reference.

Mesna, dimesna, and analogues of these compounds have been the subject of several prior pharmaceutical uses described in the literature and in prior patents, both in the United States and around the world. In addition to the cytotoxic agent protection uses, one or more of these compounds have proven effective, in vitro, against a multiplicity of biological targets, and have been effective, in vivo, in the treatment of sickle cell disease, radiation exposure, chemical agent exposure, and other uses.

Mesna, dimesna, and analogues thereof are synthesized from commonly available starting materials, using acceptable routes well known in the art. One such method involves the two-step, single pot synthetic process for making dimesna and like compounds of the following formula:

$$R_1-S-R_2;$$

wherein:

$R_1$ is hydrogen, X-lower alkyl, or X-lower alkyl-$R_3$;

$R_2$ is -lower alkyl-$R_4$;

$R_3$ and $R_4$ are each individually $SO_3M$ or $PO_3M_2$;

X is absent or X is sulfur; and

M is an alkali metal.

The process essentially involves a two-step single pot synthetic process, which results in the conversion of an alkenyl sulfonate salt or acid to the desired formula I compound. The process in the case of mesna is a single step process that converts the alkenyl sulfonate salt to mesna or a mesna derivative by reacting with an alkali metal sulfide or with hydrogen sulfide.

If the desired end product is dimesna or a dimesna analogue, a two-step single pot process is involved. Step 1 is as described above. Step 2 of the process is performed in the same reaction vessel as Step 1 without the need to purify or isolate the mesna formed during that step. Step 2 includes the introduction of oxygen gas into the vessel, along with an increase in pressure and temperature above ambient values, at least 20 pounds per square inch (psi) and at least 60° C. Dimesna or a derivative thereof is formed in essentially quantitative yield.

Other processes, well known and documented in the prior art, may be employed to make either mesna or dimesna, or derivatives and analogues thereof.

SUMMARY OF THE INVENTION

This invention involves the administration of an effective amount of a compound of formula I, below, for prevention or treatment of atherosclerosis.

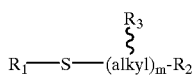
(I)

wherein:

$R_1$ is hydrogen, lower alkyl or

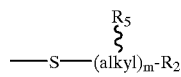

$R_2$ and $R_4$ are each individually $SO_3^-M^+$, $PO_3^{2-}M_2^{2+}$, or $PO_2S^{2-}M_2^{2+}$;

$R_3$ and $R_5$ are each individually hydrogen, hydroxy or sulfhydryl;

Each m is individually 1, 2, 3, 4, 5 or 6 with the proviso that if m is 1, then $R_3$ is hydrogen; and M is hydrogen or an alkali metal ion; or a pharmaceutically acceptable salt thereof.

Effective amounts of the formula I compounds to be administered according to the method of this invention are variable, and depend on the severity of the patient's condition or the assessed risk of the patient to develop atherosclerosis.

Accordingly, it is an object of this invention to provide for a method of safely and effectively treating a gastrointestinal disorder.

Another object is to provide a method of treating a gastrointestinal disorder by administration of a thiol or reducible disulfide to the patient in need of treatment.

Other objects will become apparent upon a reading of the following description.

DESCRIPTION OF THE PREFERRED EMBODIMENTS

The preferred embodiments herein described are not intended to be exhaustive or to limit the invention to the precise form disclosed. They are chosen and described to explain the principles of the invention, and its application and practical use to best enable others skilled in the art to follow its teachings.

The method of this invention involves the administration of an effective amount of a formula I compound to a patient at risk of developing atherosclerosis. Alternatively, the invention involves treatment of a patient having atherosclerosis by administration of an effective amount of a formula I compound. Administration may be either oral or parenteral.

The formula I compounds work to treat or prevent atherosclerosis by controlling blood plasma levels of homocysteine. As stated above, the formula I compounds form conjugates with certain thiol-containing biochemicals, which serves to lower their toxicity profiles and provide for rapid to elimination through the kidneys.

The effective amount of the formula I compound will necessarily depend upon the severity of the patient's condition or the assessed risk of the patient developing atherosclerosis. Assessed risk can be determined through the patient's medical history accompanied by a test for blood homocysteine concentrations. The higher the levels of homocysteine, the more formula I compound should be administered.

Since the formula I compounds are essentially nontoxic, large amounts can be safely administered. The preferred dosage to treat or prevent atherosclerosis may be as low as 0.1 mg/kg up to 3,000 mg/kg. The more severe the risk, the more formula I compound should be administered to provide an effective response.

Administration is preferably through parenteral or oral routes. For parenteral administration, the formula I compound is dissolved in a suitable solvent, most preferably water, to produce a solution that may be injected or infused. One or more pharmaceutically acceptable excipients may also be added to provide for an elegant formulation. Parenteral usage is favored for acute or especially severe symptoms of atherosclerosis.

For oral administration the formula I compound is preferably combined with one or more pharmaceutically acceptable excipients, fillers and/or diluents. Oral dosage forms may include pills, caplets, tablets, and others. Alternatively, the formula I compound may be contained in a deglutable container such as a gelatin capsule or the like.

The formula I compounds are hypothesized to work by conjugation of homocysteine. The conjugated form is believed to be relatively nontoxic, and of increased water solubility, which both impedes entry into cells and facilitates its elimination through the kidneys.

Administration of the formula I compound should be made as soon as possible following diagnosis of the gastrointestinal disorder, preferably immediately after the onset of symptoms. Preferred initial dose is between 10 mg/kg and 1000 mg/kg. High doses may be repeated ad libitum. Careful observation and analysis is performed regularly after diagnosis as per accepted medical procedures for treating or preventing atherosclerosis.

Other accepted methods of treatment may also be combined with the administration of the formula I compound. Due to the excellent safety profile, additional doses of the formula I compound may be administered safely if the initial dose does not produce a response.

It is understood that the above description is in no way limiting of the invention, which may be modified within the scope of the following claims.

What is claimed is:

1. A method of treating a patient afflicted with or at risk of developing atherosclerosis, said method comprising administering to the patient in need thereof an effective amount of a compound of formula I:

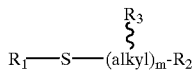

(I)

wherein:

$R_1$ is hydrogen, lower alkyl or

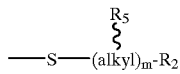

$R_2$ and $R_4$ are each individually $SO_3^-M^+$, $PO_3^{2-}M_2^{2+}$, or $PO_2S^{2-}M_2^{2+}$;

$R_3$ and $R_5$ are each individually hydrogen, hydroxy or sulfhydryl;

each m is individually 1, 2, 3, 4, 5 or 6 with the proviso that if m is 1, then $R_3$ is hydrogen; and M is hydrogen or an alkali metal ion; or a pharmaceutically acceptable salt thereof.

2. The method of claim 1 wherein the effective amount of the formula I compound administered is from 0.1 mg/kg of body weight to 3,000 mg/kg of body weight.

3. The method of claim 1 wherein the compound is administered orally.

4. The method of claim 1 wherein the compound is administered parenterally.

* * * * *